(12) United States Patent
Atanasoska et al.

(10) Patent No.: US 8,389,083 B2
(45) Date of Patent: Mar. 5, 2013

(54) POLYMER COATINGS WITH CATALYST FOR MEDICAL DEVICES

(75) Inventors: Liliana L. Atanasoska, Edina, MN (US); Shankar Godavarti, St. Paul, MN (US); Michael S. Arney, Minneapolis, MN (US); Joseph T. Delaney, Jr., Jena (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1172 days.

(21) Appl. No.: 12/253,712

(22) Filed: Oct. 17, 2008

(65) Prior Publication Data

US 2010/0100057 A1  Apr. 22, 2010

(51) Int. Cl.
*B32B 1/08* (2006.01)
*B32B 27/08* (2006.01)
*B32B 27/18* (2006.01)
*B32B 27/34* (2006.01)

(52) U.S. Cl. .................... 428/35.7; 428/420; 428/423.1; 428/474.4

(58) Field of Classification Search .................. None
See application file for complete search history.

(56) References Cited

U.S. PATENT DOCUMENTS

| | | | |
|---|---|---|---|
| 4,487,808 A * | 12/1984 | Lambert | 428/423.1 |
| 5,788,666 A | 8/1998 | Atanasoska | |
| 5,840,056 A | 11/1998 | Atanasoska | |
| 5,857,993 A | 1/1999 | Atanasoska et al. | |
| 5,871,461 A | 2/1999 | Atanasoska et al. | |
| 5,941,843 A | 8/1999 | Atanasoska et al. | |
| 6,265,037 B1 | 7/2001 | Godavarti et al. | |
| 6,280,667 B1 | 8/2001 | Koenig et al. | |
| 6,350,397 B1 | 2/2002 | Heikkila et al. | |
| 6,680,090 B2 | 1/2004 | Godavarti et al. | |
| 6,682,789 B2 | 1/2004 | Godavarti et al. | |
| 7,365,126 B2 | 4/2008 | Atanasoska et al. | |
| 7,465,777 B2 | 12/2008 | Zoromski et al. | |
| 7,470,466 B2 | 12/2008 | Ippoliti et al. | |
| 2001/0019749 A1 | 9/2001 | Godavarti et al. | |
| 2001/0051242 A1 | 12/2001 | Godavarti et al. | |
| 2001/0051243 A1 | 12/2001 | Godavarti et al. | |
| 2005/0142314 A1 | 6/2005 | Burgmeier et al. | |
| 2005/0143772 A1 | 6/2005 | Burgmeier et al. | |
| 2005/0227087 A1 | 10/2005 | Burgmeier et al. | |
| 2005/0228429 A1 | 10/2005 | Burgmeier et al. | |
| 2006/0088567 A1 | 4/2006 | Warner et al. | |
| 2006/0100696 A1 | 5/2006 | Atanasoska et al. | |
| 2006/0182907 A1 | 8/2006 | Atanasoska et al. | |
| 2006/0184092 A1 | 8/2006 | Atanasoska et al. | |
| 2006/0212106 A1 | 9/2006 | Weber et al. | |
| 2006/0230476 A1 | 10/2006 | Atanasoska et al. | |
| 2007/0048348 A1 | 3/2007 | Atanasoska et al. | |
| 2007/0066764 A1 | 3/2007 | Atanasoska et al. | |
| 2007/0067882 A1 | 3/2007 | Atanasoska et al. | |
| 2007/0072978 A1 | 3/2007 | Zoromski et al. | |
| 2007/0144124 A1 | 6/2007 | Schewe et al. | |
| 2007/0148461 A1 | 6/2007 | Ippoliti et al. | |
| 2007/0148697 A1 | 6/2007 | Delaney, Jr. et al. | |
| 2007/0149690 A1 | 6/2007 | Zoromski et al. | |
| 2007/0149743 A1 | 6/2007 | Zoromski et al. | |
| 2007/0154513 A1 | 7/2007 | Atanasoska et al. | |
| 2007/0178136 A1 | 8/2007 | Arney et al. | |
| 2007/0191814 A1 | 8/2007 | Chen et al. | |
| 2007/0191923 A1 | 8/2007 | Weber et al. | |
| 2007/0191931 A1 | 8/2007 | Weber et al. | |
| 2007/0207182 A1 | 9/2007 | Weber et al. | |
| 2007/0208155 A1 | 9/2007 | Zoromski et al. | |
| 2007/0224244 A1 | 9/2007 | Weber et al. | |
| 2007/0244569 A1 | 10/2007 | Weber et al. | |
| 2007/0264303 A1 | 11/2007 | Atanasoska et al. | |
| 2008/0004691 A1 | 1/2008 | Weber et al. | |
| 2008/0050415 A1 | 2/2008 | Atanasoska et al. | |
| 2008/0051881 A1 | 2/2008 | Feng et al. | |
| 2008/0057105 A1 | 3/2008 | Atanasoska et al. | |
| 2008/0064848 A1 | 3/2008 | Atanasoska et al. | |
| 2008/0071340 A1 | 3/2008 | Atanasoska et al. | |
| 2008/0071349 A1 | 3/2008 | Atanasoska et al. | |
| 2008/0071352 A1 | 3/2008 | Weber et al. | |
| 2008/0071353 A1 | 3/2008 | Weber et al. | |
| 2008/0071358 A1 | 3/2008 | Weber et al. | |
| 2008/0086201 A1 | 4/2008 | Weber et al. | |
| 2008/0097577 A1 | 4/2008 | Atanasoska et al. | |
| 2008/0131479 A1 | 6/2008 | Weber et al. | |
| 2008/0161906 A1 | 7/2008 | Atanasoska et al. | |
| 2008/0175881 A1 | 7/2008 | Ippoliti et al. | |
| 2008/0183277 A1 | 7/2008 | Atanasoska et al. | |
| 2008/0183278 A1 | 7/2008 | Atanasoska et al. | |

(Continued)

FOREIGN PATENT DOCUMENTS

GB      1170300      11/1969

OTHER PUBLICATIONS

International Search Report. Sep. 15, 2010. 17 pages.
Abaee, M., et al. "Efficient MgBr2.OEt2-catalyzed Knoevenagel condensation". Chem. and Chem. Eng. Research Center of Iran, ARKIVOC 2006 (xv) pp. 48-52.
Boulares, A., et al. "Synthesis and characterization of poly (copolyethers-block-polyamides) . . . ". Polymer 41 (2000), pp. 3561-3580.
He, Z., et al. "A Selective Catalyst for Two Component Waterborne Polyurethane Coatings". International Waterborne . . . Symposium, Feb. 1999, 15 pgs.
Heijkants, R., et al. "Extruder synthesis of a new class of polyurethanes: . . . ". Polymer 46 (2005), pp. 8981-8989.
Jayabalan, M., et al. "In vivo biocompatibility of aliphatic segmented polyurethane in rabbit". J. Biosco., vol. 14, No. 3, Sep. 1989, pp. 289-299.

(Continued)

*Primary Examiner* — Ramsey Zacharia
(74) *Attorney, Agent, or Firm* — Brooks, Cameron & Huebsch, PLLC

(57) ABSTRACT

Coating compositions and coatings for medical devices formed from the coating compositions that include a catalyst in a support polymer, where the support polymer helps to support and retain the catalyst in the coating on the medical device. The catalyst in the support polymer can act to chemically bond specific compounds migrating from a body of the medical device formed from a polymer to at least one of the polymer and/or other specific compounds migrating from the body of the medical device.

15 Claims, No Drawings

U.S. PATENT DOCUMENTS

| | | | |
|---|---|---|---|
| 2008/0188825 | A1 | 8/2008 | Atanasoska et al. |
| 2008/0188836 | A1 | 8/2008 | Weber et al. |
| 2008/0249600 | A1 | 10/2008 | Atanasoska et al. |
| 2008/0262412 | A1 | 10/2008 | Atanasoska et al. |
| 2008/0287984 | A1 | 11/2008 | Weber et al. |
| 2008/0314941 | A1 | 12/2008 | Knych et al. |
| 2009/0029077 | A1 | 1/2009 | Atanasoska et al. |
| 2009/0048659 | A1 | 2/2009 | Weber et al. |
| 2009/0062483 | A1 | 3/2009 | Ippoliti et al. |

OTHER PUBLICATIONS

Kung, Harold, et al. "Preparation of oxide catalysts and catalyst supports . . . ". The Chem. Eng. Journal, 64 (1996), pp. 203-214.

Majumdar, Partha, et al. "Influence of solvent composition and degree of reaction on the formation . . . ". Polymer 47 (2006), pp. 4172-4181.

Molero, Carolina, et al. "Recovery of polyols from flexible polyurethane foam . . . ". Polymer Degradation and Stability 91 (2006), pp. 894-901.

Ostah, Naaman, et al. "Investigation of amine and polyol functionality in extracts . . . ". Analyst 125 (2000), pp. 111-114.

Rokicki, Gabriel, et al. "A new route to polyurethanes from ethylene . . . ". Polymer 43 (2002), pp. 2927-2935.

Schmitz, Frank, et al. "Coplymerization of 2,2-dimethyltrimethylene carbonate . . . ". Polymer, vol. 39, No. 14 (1998), pp. 3197-3186.

Spaans, C., et al. "A new biomedical polyurethane with a high modulus based on . . . ". J. of Materials Science: Materials in Medicine, vol. 9(1998), pp. 675-678.

Yang, Shuguang, et al. "Composite Thin Film by Hydrogen-Bonding Assembly . . . ".Langmuir (2006), pp. 338-343.

Deleuze, H., et al. "Reactivity of some polymer-supported titanium catalysts in transesterification . . . " Journal of Molecular Catalysis A, Chemical 159, (2000), pp. 257-267.

Munchow, V., et al. "Poly[(oligoethylene glycol) dihydroxytitanate] as organic-inorganic polymer-electrolytes." Electrochima Acta 45 (2000), pp. 1211-1221.

Lamaka, S., et al. "TiOx self-assembled networks prepared by templating approach as nanostructured reserviours for . . . " Electrochemistry Communications 8, (2006), pp. 421-428.

Udipi, Kishore, et al. "Polyamides from lactams via anionic ring-opening polymerization: 1. Chemistry and some recent findins*." Polymer, vol. 38, No. 4 (1997), pp. 927-938.

* cited by examiner

POLYMER COATINGS WITH CATALYST FOR MEDICAL DEVICES

FIELD OF THE DISCLOSURE

The present disclosure relates to coatings for medical devices and in particular to polymer coatings with a catalyst for medical devices.

BACKGROUND

Advances in the design of medical devices such as balloon catheters, guide wires and stents have greatly improved the quality of medical care. Many of the advances in medical devices have been in the area of coatings for medical devices. Coatings can provide a wide range of design options and related advances in performance for the medical device. For example, advances in coatings have lead to better lubricity and wettability, passivity against protein absorption, antimicrobial properties, drug delivery, biocompatibility and hemocompatibility for the medical device.

Polymeric coatings have been used to modify the surfaces of medical devices. Polymeric coatings can be chemically, mechanically and physically tailored to produce the desired combination of properties and have found use for nonthrombogenic, lubricous, anti-microbial and protective purposes. Such materials can be applied to devices from solvent, from aqueous solution or from the vapor phase. Alone, in combination, or as carriers for active pharmaceutical ingredients, polymeric coatings continue to enable an ever-expanding market for implantable medical devices.

There is, however, a need for further advances in the design and implementation of coatings for use with medical devices.

SUMMARY

The present disclosure provides coating compositions and coatings for medical devices formed from the coating compositions. The coating compositions and the coatings formed from the compositions include a catalyst in a support polymer, where the support polymer helps to support and retain the catalyst in the coating on the medical device. The catalyst in the support polymer can act to chemically bond specific compounds migrating from a body of the medical device formed from a polymer to at least one of the polymer and/or other specific compounds migrating from the body of the medical device.

For the various embodiments, specific compounds in the body formed from the polymer of the medical device can include free oligomer compounds and free monomer compounds. These compounds can be formed initially in the manufacture of the polymer used to form the body and/or formed during the manufacture of the medical device as the result of various degradation process, as will be discussed herein. Under certain conditions, as discussed herein, the free oligomer and free monomer compounds present in the body of the medical device can migrate from and/or through the polymer towards and/or to a surface the medical device.

For the various embodiments, the coating of the present disclosure can be formed over at least a portion of the surface of the medical device. The catalyst supported and retained in the support polymer of the coating can act to chemically bond the free oligomer compounds and/or the free monomer compounds that migrate from the body toward and/or to the surface of the body to either themselves (i.e., other free oligomer and/or monomer compounds) and/or to the polymer forming the body of the medical device.

So, for example, the catalyst can act to form at least one of a homopolymer and a co-polymer with the free oligomer compounds and/or the free monomer compounds that migrate toward and/or the surface of the body of the medical device. In an additional embodiment, the catalyst can act to chemically bond the free oligomer compounds and/or the free monomer compounds that migrate toward and/or to the surface of the body to available reactive groups in the polymer forming the body.

For the various embodiments, a variety of catalysts for use with the coating of the present disclosure are possible. For example, useful catalysts can include, but are not limited to, those selected from at least one of a metal alkoxide, a Grignard reagent, and combinations thereof. With respect to metal alkoxides, these can be selected from at least one of $Al(OR)_3$, $Ti(OR)_4$, $Zr(OR)_4$, $Mg(OR)_2$, and combinations thereof, where R is an C1 to C4 alkyl group (linear and/or branched), and the Grignard reagent can be selected from at least one of an alkyl-MgBr, an aryl-MgBr, a $MgBr_2$-diethyl etherate ($MgBr_2.OEt_2$), and combinations thereof.

For the various embodiments, the support polymer for the coating can be selected from at least one of polyether block amide, polytetramethylene ether glycol (PTMEG), polystyrene, polyether, polyurethane, poly(ethylene oxide), and combinations thereof. Other support polymers are also possible.

For the various embodiments, the free oligomer compounds and the free monomer compounds can include a variety of compounds and/or chemical groups that can be used to chemically bond these specific compounds either to themselves and/or to the available reactive groups in the polymer forming the body of the medical device. For example, the free oligomer compounds and/or the free monomer compounds can include an amide group. In addition, at least one of the free oligomer compounds and/or the free monomer compounds can include a lactam compound (i.e., a cyclic amide), for example the monomer laurolactam, or one of its oligomers.

Alternatively, at least one of the free oligomer compounds and/or the free monomer compounds can include a methylene diphenyl diisocyanate compound. Other compounds and/or chemical groups of the free oligomer compounds and/or the free monomer compounds are also possible. As appreciated, once the available reactive groups of the polymer, the free oligomer compounds and/or the free monomer compounds are known, the catalyst and the support polymer of the coating can be selected to allow for chemically bonding these specific compounds to either themselves and/or the polymer of the medical device.

The coatings of the present disclosure can further provide other potential improvements in functionality to the medical device. For example, in some embodiments, the medical device can further include a hydrophilic coating over at least a portion of the coating of the present disclosure. The medical device can further include a coating formed from a sol-gel process between the hydrophilic coating and the coating formed from the catalyst and the support polymer.

The coatings of the present disclosure can be used for a variety of medical devices. For example, the medical device can be a body of an electrically conductive lead. In an additional embodiment, the medical device is a catheter body of a balloon catheter. For the various embodiments, the balloon catheter can include an elongate body formed with a polyether block amide polymer. The elongate body has a surface and free oligomer compounds and free monomer compounds in the polyether block amide polymer, where the free oligomer compounds and free monomer compounds include a laurolactam compound that migrate to the surface of the elongate body. A coating of the present disclosure is present over at least a portion of the surface of the elongate body, where the coating is formed from the support polymer and a catalyst having a metal alkoxide and a Grignard reagent, where the catalyst acts to chemically bond the free oligomer compounds and the free monomer compounds that migrate to the surface of the body. Using the coating of the present disclosure on other medical devices is also possible.

Embodiments of the present disclosure also provide for methods of both forming the coating of the present disclosure and using the coating of the present disclosure. For example, embodiments of the present disclosure can include a method of fixing free oligomer compounds and/or free monomer compounds in the body formed from the polymer of a medical device. Such embodiments can include providing a body formed from the polymer, the body having the free oligomer compounds and the free monomer compounds in the polymer; forming a coating over at least a portion of the polymer of the body with a support polymer; and chemically bonding a catalyst in the support polymer, where the catalyst acts to chemically bond the free oligomer compounds and the free monomer compounds that encounter the catalyst in the support polymer.

The above summary of the present disclosure is not intended to describe each disclosed embodiment or every implementation of the present disclosure. The description that follows more particularly exemplifies illustrative embodiments. In several places throughout the application, guidance is provided through various embodiments, where the embodiments can be used in various combinations. In each instance, the recited embodiments serve only as a representative group, and should not be interpreted as an exclusive list.

Definitions

As used herein, the term "free oligomer compounds" includes oligomers formed from a small plurality of monomer units derived from molecules of lower relative molecular mass. The small plurality of units can include two, three and/or four monomer units.

As used herein, the term "free monomer compounds" includes a molecule or compound that is capable of conversion to a polymer, a synthetic resin, or an elastomer by combination with itself or other similar compound or molecule.

As used herein, the term "catalyst" can include substances that affect the rate of a chemical reaction without itself necessarily being consumed or undergoing a chemical change and/or substances that act as activators and initiators in polymerization reactions. Such catalysts can be organic compounds, inorganic compounds and/or organoinetallic compounds.

As used herein, the term "particle" includes an aggregation of specific compounds that migrate from a body of a medical device to the surface of the medical device.

The term "and/or" means one, one or more, or all of the listed elements.

As used herein, "a," "an," "the," "at least one," and "one or more" are used interchangeably. The terms "includes" and "comprises" and variations thereof do not have a limiting meaning where these terms appear in the description and claims. Thus, for example, a coating composition that includes "a" catalyst can be interpreted to mean that the catalyst includes "one or more" catalysts.

DETAILED DESCRIPTION

The present disclosure provides coating compositions and coatings for medical devices formed from the coating compositions. The coating compositions and the coatings formed from the coating compositions include a catalyst in a support polymer, where the support polymer helps to support and retain the catalyst in the coating on the medical device. The catalyst in the support polymer of the coating can act to chemically bond specific compounds migrating from a body formed from a polymer of the medical device to at least one of the polymer of the body and/or other specific compounds migrating from the body of the medical device.

As discussed herein, chemically bonding these specific compounds as provided herein can help to prevent the specific compounds from aggregating as particles on the surface of the medical device. Preventing the aggregation of such particles in and/or on the medical device may help to minimize undesirable side effects that can result from the presence of such particles and/or the specific compound in a biological environment. Such undesired side effects can include, but are not limited to, thrombogenic or embolic effects caused at least in part by the presence of such particles and/or the specific compounds.

Embodiments of the present disclosure include a medical device having a body formed at least in part from a polymer. The present disclosure provides embodiments in which the coating having the catalyst in the support polymer can be formed over at least a portion of a surface of the body formed from the polymer. As the specific compounds migrate through the body formed from the polymer of the medical device toward the surface of the body the catalyst in the support polymer can act to polymerize the specific compounds to either themselves, in the form of relatively larger compounds (e.g., at least one of a homopolymer and/or a copolymer), and/or to available reactive groups on the polymer of the body.

For the various embodiments, the specific compounds can be present in the polymer of the body forming at least a part of the medical device as free monomer compounds, free oligomer compounds, as degradation products resulting from processing of the medical device, and/or as a combination of these compounds. For the various embodiments, the free monomer compounds and/or the free oligomer compounds can be present in the body of the medical device as a byproduct of the polymerization process used in forming the polymer. For the various embodiments, the degradation of the polymer forming the body of the medical device during an extrusion process can be caused at least in part to the processing conditions used in forming the body of the medical device. For the various embodiments, the degradation products of the polymer can include a variety of oligomer compounds and/or monomer compounds.

The specific compounds can then migrate through the body of the medical device towards and/or to the surface of the body. The tendency of the specific compounds to migrate may be attributable to a number of different driving factors, including, but not limited to, gradations in material density, osmotic pressure, the hydrophilic or hydrophobic nature and/or the relatively low molecular weight of the specific compounds. For example, it is possible for one or more of the monomer and/or oligomer compounds to "bloom" from the polymer on the surface of the body of the medical device under the influence of both temperature and moisture. Once at or near the surface, the monomer and/or oligomer compounds can aggregate to form particles on the surface of the medical device. Formation of such particles has been associated with undesirable side effects in a biological environment.

For the various embodiments, the body of medical devices can be formed from a thermoplastic polymer that include specific compounds, as discussed herein, that can migrate toward and/or to a surface of the body. As appreciated, a variety of polymers used for the body of medical devices may include specific compounds that, when used in vivo, may lead to undesirable biological side effects.

An example of such a polymer includes nylon block copolymers. Generally, nylon block copolymers can be alternating blocks of polyamide segments and other segments such as segments of polymers such as polyethers, polyesters, hydrocarbons and/or polysiloxanes. These nylon block copolymers are generally prepared by copolymerizing a lactam monomer in the presence of the polymers component. Lactam monomers can include, but are not limited to, laurolactam (found mostly in nylon 12), ϵ-caprolactam, δ-valerolactam, among others. For the various embodiments, the free oligomer compounds and the free monomer compounds can include amide groups, such as the lactam compound and in particular the laurolactam compound.

Specific examples of a nylon block copolymer include those sold under the tradename PEBAX®. The PEBAX® copolymers consist generally of polyether blocks separated by polyamide blocks. The polyether blocks can be based upon polyethylene glycol, polypropylene glycol, or polytetramethylene ether glycol. The polyamides are usually based upon nylon 12 and/or nylon 11, but can be based upon nylons 6 of nylon-6,6 or even a copolymers of different nylons. A wide range of block polyamides have been offered and vary in the type of polyether, the nature of the polyamide block and the ratio of polyether to polyamide blocks. Polyether block amino is used in a wide variety of medical devices.

Many medical devices that have nylon block copolymers in their body also have a hydrophilic coating over the body of the medical device. The action of the hydrophilic coating on the body of the medical device can result in moisture being present at the interface and in contact with the polyether block amine. The moisture in turn serves to mobilize lactam monomers and/or crystals of the lactam monomers present in the elastomeric nylon block copolymer. For example, PEBAX® copolymers have amide oligomer or monomer specific compounds, such as lactam monomers and/or crystals, either as remaining un-reacted species and/or as a result of extrusion-induced degradation. Over time, these specific compounds can phase separate and migrate to the surface of the body. For example, this separation and migration can occur from the body of the medical device during the sterilization process, where high temperatures and moisture can result particle formation on the surface of the body.

An additional example of a thermoplastic used to form a body that may include specific compounds that can migrate to the surface of the medical device includes polyurethanes. Polyurethanes are generally formed by reacting a polyisocyante containing monomer (e.g., a diisocyonate) with a polyalcohol containing monomer (e.g., a polyol) in the presence of a catalyst, along with other additives. Polyisocyanates can include aromatics such as methyl diphenyl diiocyanate (MDI) and toluene diisocyante, and aliphaties such as hexamethylene diisocyanate and isophorone diisocyanate.

A particularly useful diisocyante monomer used in the production of medical devices includes, but is not limited to, MDI. MDI is a specific compound that while useful in forming polyurethanes, can also be included as at least one of the free oligomer compounds and/or the free monomer compounds in the body of the medical device formed with the polyurethane. Over time, the MDI can phase separate from the surrounding material and migrate to the surface of the body of the medical device where it may lead to undesirable biological side effects. For example, this separation and migration of the MDI can occur from the body of the medical device in and around the location of pacing electrodes and/or defibrillation electrodes on electrically conductive leads.

For the various embodiments, the coating formed with the coating composition of the present disclosure can act on one or more of the specific compounds, as discussed herein, that migrate to the surface by chemically bonding and/or cross-linking them into stable co-polymers and/or homopolymers. As discussed herein, the catalyst of the coating can act to chemically bond the specific compounds migrating from the body formed from the polymer of the medical device to at least one of the polymer of the body and/or other specific compounds migrating from the body of the medical device. The coating formed with the coating composition of the present disclosure can also function as a barrier (e.g., a physical barrier) to the specific compounds trying to migrate to the surface of the body of the medical device.

For the various embodiments, the coating includes the support polymer in which the catalyst is dispersed in a polymer network of the support polymer and/or immobilized to the support polymer through chemical bonds or weak interactions such as hydrogen bonds or donor-acceptor interactions. For the various embodiments, the support polymer can be formed with a morphology that both allows for supporting the catalyst, allowing for the catalytic reactions to occur and to help retain the catalyst in the matrix of the support polymer. For the various embodiments, the support polymer of the coating allows for the catalyst to be retained while preferentially minimizing the effect on the catalytic activity (e.g., the active points) active sites of the catalysts.

For the various embodiments, the polymer composition of the support polymer can have a glass transition temperature (Tg) in a range that allows a compliant coating to be formed on the surface of the medical device. For the various embodiments, the support polymer can have a Tg in range of about −40° C. to about 0° C. Tg of the support polymer can be measured by a suitable technique, such as dilatometry, refractive index, differential scanning calorimetry, dynamic mechanical measurement, and/or dielectric measurement.

For the various embodiments, the support polymer can be selected from at least one of polyether block amide, polytetramethylene ether glycol (PTMEG), polystyrene, polyether, polyurethane, and poly(ethylene oxide). Blends of two or more of these polymers are also possible for the support polymer. Blends can be prepared to have a Tg in the ranges as described herein. As appreciated, other polymers could also be used with the ones provided herein, where such polymers would be those that can be blended under the same or similar conditions as those used for the polymers listed herein.

In additional embodiments, functional groups on one or more of the support polymers can be used to add additional structure to the support polymer. For example, the end groups of one or more of the support polymers could be used in a chain extending reaction to produce copolymers having specific linkages that could be used in subsequent reactions for chemically bonding the catalyst.

For the various embodiments, the catalyst can act to chemically bond the free oligomer compounds and the free monomer compounds (i.e., the specific compounds) that migrate to the surface of the body. For example, the catalyst can act to chemically bond the free oligomer compounds and the free monomer compounds that migrate to the surface of the body to form at least one of a homopolymer and a co-polymer from the free oligomer compounds and the free monomer compounds.

In another example, the catalyst can act to chemically bond the free oligomer compounds and the free monomer compounds that migrate to the surface of the body to reactive groups of the polymer of the body. For the various embodiments, such a surface grafting process can occur when the polymer at the surface of the body has been chemically modified by generation of active sites on the macromolecules of the polymer that can lead to initiation of a graft polymerization or a grafting reaction. So, it is possible for the catalyst to not only chemically bond the specific compounds to form at least one of a homopolymer and/or a copolymer from the specific compounds, but also to chemically bond these specific compounds to reactive groups present on the macromolecules forming the polymer.

For the various embodiments, the catalyst used with the coating can be selected from at least one of a metal alkoxide, a Grignard reagent, and combinations thereof. For the various embodiments, the metal alkoxide can be selected from at least one of $Al(OR)_3$, $Ti(OR)_4$, $Zr(OR)_4$, $Mg(OR)_2$, and combinations thereof, where R is an C1 to C4 alkyl group, and the Grignard reagent is selected from at least one of an alkyl-MgBr, an aryl-MgBr, a MgBr-diethyl etherate, and combinations thereof. For the various embodiments, the preferred Grignard reagent is the alkyl-MgBr. Catalyst promoters can also be used with the catalyst to help maintain the effectiveness of the catalyst.

Additional catalysts can include, but are not limited to, those used in the production of polyurethanes. These can include amine compounds and/or organometallic complexes. Examples of such catalysts include, but are not limited to, metal diketonates, such as zirconium diketonate; dibutyltin dilaurate; stannous octoate; zinc octoate; diethanolamine; and/or titanium n-butoxide. Other catalysts can include triethylenediamine, dimethylcyclohexylamine, dimethylethanolamine, tetrmethylbutanediamine, pentamethyldipropylenetriamine, N-(3-dimethylaminopropyl)-N,N-diisopropanolamine, triethylamine, pentamethyldiethylenetriamine, benzyldimethylamine, N,N,N'-trimethyl-N'-hydroxyethyl-bis(aminoethyl)ether, N'-(3-(dimethylamino)propyl)-N,N-dimethyl-1,3-propanediamine. In addition, other organometallic compounds based on lead, tin, bismuth (bismuth octanoate), and zinc can be used as the polyurethane catalysts.

For the various embodiments, the coating of the present disclosure can be formed in a number of different ways and have a number of different configurations. For example, a sol-gel process can be used to form the coating of the present disclosure on the body of the medical device. For the various embodiments, the sol-gel process can be carried out in a number of techniques, including dip-coating, spray coating, spin-coating, roll-coating, among others.

In one example of a sol-gel process, a liquid solution of the catalyst, one or more polymers and an organometallic precursor (e.g., one or more of the metal alkoxides discussed herein) can be suspended in a suitable solvent, such as an alcohol (e.g., ethanol). The body of the medical device, as discussed herein, can then be coated with the liquid solution, which subsequently undergoes the hydrolysis and condensation reactions of the sol-gel process to form the support polymer (in this case an organic/inorganic continuous network) that entraps the catalyst. A thermal treatment may subsequently be used to further the polycondendsation reaction and enhance mechanic properties of the coating.

For the various embodiments, one or more polymers used in forming the support polymer can be selected to be compatible with the polymer forming the body of the medical device. So, for example, when a PEBAX® copolymer is used in forming the body of the medical device then the same PEBAX® copolymer, or comparable polymer such as a polyimide type copolymer, can be used in forming the support polymer of the coating. For the various embodiments, the solvent used with the sol-gel process can also help to facilitate the adhesion of the coating to the underlying body of the medical device. For example, the use of an alcohol in the coating composition discussed herein can help to soften and/or dissolve an outer layer of the underlying PEBAX® copolymer of the body to allow the coating to intermix and provide good adhesion at the interface of the body.

In an additional embodiment, the polymer used in support polymer can be alkoxylated polyols, such as neopentyl glycol and other low molecular weight glycols. For the various embodiments, the alkoxylated polyols used in the support polymer can be cross-linked to form a meshed network that helps to entrap and hold the catalyst of the coating. The alkoxylated polyols can also help to provide a hydrophilic property to the coating.

Prior to disposing the coating composition on the surface of the medical device, the medical device can be cleaned using a suitable technique. It is understood that while extensive cleaning processes are not required to be performed prior to forming the coating, they nonetheless can be performed, if desired.

For the various embodiments, the coating method can provide the coating with a thickness that can be affected by changing the concentration of the polymer and/or the organometallic precursors in the coating solution. That is, increasing the concentration of the polymer and/or the organometallic precursors can provide a thicker coating, while decreasing the concentration can provide a thinner coating. The coating of the present disclosure can also be highly compliant and conformal, meaning that it shapes well to the body of the medical device on which it has be formed and that it can form to the changes in the shape of the body without introducing a substantial physical deformities.

For the various embodiments, the coating of the present disclosure can have a multi-layer construction. For the various embodiments, the multi-layer construction can allow for one or more of the catalysts, polymers and/or organometallic precursors to be used in forming different layers of the coating. In addition, layers with other functional properties can be used with the coating of the present disclosure. For example, layers can provide gradient, hydrophilic, and/or drug-delivery properties to the coating of the present disclosure. The suitability of the coating composition and the use of the multi-layer construction for use with a particular medical device can be evaluated by those skilled in the art, given the present description.

For the various embodiments, the multilayer construction can be formed by applying each of the layers successively. For example, the multi-layer coating can be formed by successive applications of the sol-gel process, where each of the successive layers can be formed with compositions that are either the same or different than the preceding layer.

For example, the multilayer construction can allow a hydrophilic coating to be formed over at least a portion of the coating of the present disclosure to change the lubricity properties of the medical device. For the various embodiments, the hydrophilic coating can be formed using a hydrophilic polymer that can be a copolymer or a homopolymer. As used herein, the term "hydrophilic" refers to a polymer that is water-loving; typically, the hydrophilic polymers swell in the presence of water. The hydrophilic polymer that is used to form the hydrophilic coating can be a synthetic polymer, a natural polymer, or a derivative of a natural polymer. Examples of suitable hydrophilic polymers for use in the hydrophilic coating can include, but are not limited to, polyethylene oxide, PEBAX® copolymers, and combinations thereof. Other hydrophilic polymers are also possible.

For the various embodiments, the hydrophilic coating can be formed using a sol-gel process, as discussed herein, where the coating composition used in the sol-gel process may or may not include the catalyst. Use of the sol-gel process also allows for a gradient to be formed in the hydrophilic coating. For example, the sol-gel process could be used to provide two or more layers of the hydrophilic coating, where the layers can provide either an increase or a decrease in the concentration of the hydrophilic polymer and/or a change in the hydrophilic polymer used in the hydrophilic coating.

In an alternative embodiment, a hydrophilic polymer could be used in the coating composition as discussed herein. So, the coating of the present disclosure would then also provide hydrophilic properties in addition to the catalytic properties discussed herein. For the various embodiments, multi-layer sol-gel coating techniques as discussed herein can be used to modify the hydrophilic properties of the coating of the present disclosure. For example, a hydrophilic gradient can be provided in the coating of the present disclosure.

For the various embodiments, the hydrophilic gradient can diminish as the coating extends away from the surface of the body. In an additional embodiment, the hydiophilic gradient can first diminish as the coating extends away from the surface of the body then increase again. For the various embodiments, this multi-layer configuration allows the coating to transition from being hydrophilic to hydrophobic and then, optionally, back to being hydrophilic. Introducing the hydrophobic property into the coating can help to provide a barrier function to the specific compounds that can migrate from the body of the medical device. Other combinations and permutations to the changes in the concentration gradient of the hydrophilic coating are also possible.

For the various embodiments, a gradient in the concentration of the catalyst can also be formed in the coating of the present disclosure. For example, the sol-gel process discussed herein can be used to form a multi-layer structure in which the concentration of the catalyst can change as the coating extends away from the surface of the body of the medical device. So, for example, a concentration gradient of the catalyst can be formed in the coating that diminishes as the coating extends from a surface of the body. As appreciated, changes in the concentration gradient of both the catalyst and the hydrophilic properties of the polymer used in the polymer support, as discussed herein, can also be made to coating.

In an additional embodiment, the medical device can further include an intermediate coating formed from a sol-gel process between a hydrophilic coating, as discussed herein, and the coating formed with the catalyst and the support polymer as discussed herein. For example, the intermediate coating can include one or more polymers that impart a more hydrophobic property to the intermediate coating as compared to either of the coating having the catalyst and the support polymer or the hydrophilic coating. For the various embodiments, this intermediate coating can act as a barrier layer to the migration of the specific compounds from the body of the medical device.

In some embodiments, a latent reactive group may also be included in the polymer used in the coating of the present disclosure. For the various embodiments, the latent reactive group can be activated in a step in the coating method to form covalent bonds between one or more components of the coating. For example, the latent reactive groups could be use to chemically bond the catalyst to the polymer of the support polymer. For the various embodiments, the latent reactive groups may also be used to bond the hydrophilic polymers of hydrophilic coating to the polymer of the coating underlying the hydrophilic coating.

For the various embodiments, the latent reactive group can be provided as a separate component that is independent of the coating. For example, the latent reactive group can be a photoreactive cross-linking agent, as are known. In other embodiments, the latent reactive group can be part of the coating, for example, as a reactive group pendent from the polymer of the coating. In yet other embodiments, the coating can be formed from latent reactive groups that are both pendent from and independent of the hydrophilic polymer. Attachment of such photoreactive group can be achieved by, for example, substitution or addition reactions to the polymer of the coating.

One or more other optional materials, such as other polymers, can be present in the coating composition of the present disclosure. Other, optional additional components, which can be non-polymeric, can be present in the coating composition, such as those that improve the formation of the coating. These optional additional components can include, for example, bioactive agents, which can also be included and released from the coating. Exemplary bioactive agents include, but are not limited to, antibiotics, anti-inflammatory agents, anti-proliferative agents, immunomodulatory agents, anti-mitotics and anesthetics.

The coating compositions of the present disclosure are particularly suitable for providing a coating on a medical devices that include a body formed from a polymer, as discussed herein. For the various embodiments, the body formed from the polymer can have the form of a layer of a variety of thicknesses over a substructure. In other embodiments, a majority (including the entirety) of the body of the medical device can be formed from the polymer. For the various embodiments, the coating of the present disclosure may also be formed from the coating compositions on a number of other materials (e.g., non-polymer materials) and/or medical devices.

For the various embodiments, the medical device can be used in such a way as to be introduced temporarily or permanently into a mammal for the prophylaxis or treatment of a medical condition. Such medical devices can be introduced subcutaneously, percutaneously or surgically to rest within an organ, tissue, or lumen of an organ, such as arteries, veins, ventricles, or the arteries and/or veins of the heart.

The coating composition of the present disclosure can be utilized to form a coating for a variety of medical devices for which it is desired to provide a functional coating at a surface thereof. Exemplary medical devices include catheters, a catheter body of a balloon catheter, other vascular devices (e.g., grafts, valves, artificial hearts, heart assist devices); implantable defibrillators; blood oxygenator devices (e.g., tubing, membranes); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); membranes; cell culture devices; chromatographic support materials; biosensors; shunts for hydrocephalus; wound management devices; endoscopic devices; infection control devices; orthopedic devices (e.g., for joint implants, fracture repairs); dental devices (e.g., dental implants, fracture repair devices); urological devices (e.g., penile, sphincter, urethral, bladder and renal devices, and catheters); colostomy bag attachment devices; ophthalmic devices; glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts).

Other medical devices can include urinary catheters, intravenous catheters, small diameter grafts, vascular grafts, artificial lung catheters, septal defect closure devices (e.g., atrial septal defect), a lead body of an electrically conductive lead for cardiac rhythm management (e.g., pacer leads, defibrillation leads), glucose sensors (long-term and short-term), degradable coronary stents (e.g., degradable, non-degradable, peripheral), blood pressure and stent graft catheters, birth control devices, benign prostate and prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches.

Other medical devices include, but are not limited to, vena cava filters, urinary dialators, endoscopic surgical tissue extractors, atherectomy catheters, clot extraction catheters, percutaneous transluminal angioplasty catheters (PTCA catheters), stylets (vascular and non-vascular), guidewires (such as coronary guidewires), drug infusion catheters, esophageal stents, circulatory support systems, angiographic catheters, transition sheaths and dialators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

Other medical devices suitable for the present disclosure include, but are not limited to catheters (including vascular or urinary), guidewires, implantable vascular access ports, blood storage bags, vascular stents, blood tubing, vascular grafts, intraaortic balloon pumps, cardiovascular sutures, total artificial hearts and ventricular assist pumps, extracorporeal devices such as blood oxygenators, blood filters, hemodialysis molecules, hemoperfusion molecules, plasmapheresis molecules, hybrid artificial organs such as pancreas or liver and artificial lungs, as well as filters adapted for deployment in a blood vessel in order to trap emboli (also known as "distal protection devices").

The embodiments of the present disclosure are not intended to be exhaustive or to limit the disclosure to the precise forms disclosed in the following detailed description. Rather, the embodiments are chosen and described so that others skilled in the art can appreciate and understand the principles and practices of the embodiments of the present disclosure.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments set forth herein and that such embodiments are presented by way of example only with the scope of the disclosure intended to be limited only by the claims set forth herein as follows.

What is claimed is:

1. A medical device, comprising:
   a body formed from a polymer, the body having a surface and free oligomer compounds and free monomer compounds in the polymer that migrate to the surface of the body, where at least one of the free oligomer compounds and the free monomer compounds includes a lactam compound; and
   a coating over at least a portion of the surface, where the coating is formed from a catalyst and a support polymer, where the catalyst acts to chemically bond the free oligomer compounds and the free monomer compounds that migrate to the surface of the body.

2. The medical device of claim 1, where the catalyst acts to chemically bond the free oligomer compounds and the free monomer compounds that migrate to the surface of the body to form at least one of a homopolymer and a co-polymer from the free oligomer compounds and the free monomer compounds.

3. The medical device of claim 1, where the catalyst acts to chemically bond the free oligomer compounds and the free monomer compounds that migrate to the surface of the body to reactive groups of the polymer of the body.

4. The medical device of claim 1, where the free oligomer compounds and the free monomer compounds include an amide group.

5. The medical device of claim 1, where the lactam compound is a laurolactam compound.

6. The medical device of claim 1, where the catalyst is selected from at least one of a metal alkoxide, a Grignard reagent, and combinations thereof.

7. The medical device of claim 6, where the metal alkoxide is selected from at least one of $Al(OR)_3$, $Ti(OR)_4$, $Zr(OR)_4$, $Mg(OR)_2$, and combinations thereof, where R is an C1 to C4 alkyl group, and the Grignard reagent is selected from at least one of an alkyl-MgBr, an aryl-MgBr, a MgBr-diethyl etherate, and combinations thereof.

8. The medical device of claim 1, where the support polymer is selected from at least one of polyether block amide, polytetramethylene ether glycol, polystyrene, polyether, polyurethane, and poly(ethylene oxide).

9. The medical device of claim 1, where the medical device further includes a hydrophilic coating over at least a portion of the coating.

10. The medical device of claim 9, where the medical device further includes a coating formed from a sol-gel process between the hydrophilic coating and the coating formed from the catalyst and the support polymer.

11. The medical device of claim 1, where the coating provides a concentration gradient of the catalyst that diminishes as the coating extends from the surface of the body.

12. The medical device of claim 1, where the support polymer includes a hydrophilic gradient that that diminishes as the coating extends from the surface of the body.

13. The medical device of claim 1, where the medical device is a catheter body of a balloon catheter.

14. The medical device of claim 1, where the medical device is a lead body of an electrically conductive lead.

15. A catheter body of a balloon catheter, comprising:
   an elongate body formed with a polyether block amide polymer, the elongate body having a surface and free oligomer compounds and free monomer compounds in the polyether block amide polymer, where the free oligomer compounds and free monomer compounds include a laurolactam compound that migrate to the surface of the elongate body; and a coating over at least a portion of the surface of the elongate body, where the coating is formed from a support polymer and a catalyst consisting of a metal alkoxide and a Grignard reagent, where the catalyst acts to chemically bond the free oligomer compounds and the free monomer compounds that migrate to the surface of the body.

* * * * *